United States Patent [19]

van der Vies

[11] 4,147,783

[45] * Apr. 3, 1979

[54] ORAL PHARMACEUTICAL PREPARATION

[75] Inventor: Johannes van der Vies, Oss, Netherlands

[73] Assignee: Akzona Incorporated, Asheville, N.C.

[ * ] Notice: The portion of the term of this patent subsequent to Jul. 4, 1995, has been disclaimed.

[21] Appl. No.: 850,181

[22] Filed: Nov. 10, 1977

Related U.S. Application Data

[63] Continuation of Ser. No. 691,103, May 28, 1976, Pat. No. 4,098,802, which is a continuation-in-part of Ser. No. 550,397, Feb. 18, 1975, abandoned.

[30] Foreign Application Priority Data

Feb. 28, 1976 [NL] Netherlands ..................... 7402689

[51] Int. Cl.$^2$ ............................................. A61K 31/56
[52] U.S. Cl. .................................. 424/243; 260/397.4
[58] Field of Search ...................... 424/243; 260/397.4

[56] References Cited

PUBLICATIONS

Gould et al., "J.A.C.S.", vol. 79, (1957), pp. 4472–4475.
"Steroid Drugs", by Applezweig, (1962), pp. 561 and 559.

*Primary Examiner*—Elbert L. Roberts
*Attorney, Agent, or Firm*—Robert H. Falk; Charles A. Wendel; Francis W. Young

[57] ABSTRACT

The invention relates to an oral pharmaceutical preparation with androgenic activity on the basis of one or more esters of testosterone and/or 5α-dihydrotestosterone, the ester group of which has been derived exclusively from aliphatic carboxylic acids having 9–16 carbon atoms, preferably 10–12 carbon atoms in combination with a non-steroidal lipoid. The preparation may additionally contain a progestational steroid, an oestrogen or a precursor of an A-aromatic steroid.

11 Claims, No Drawings

ORAL PHARMACEUTICAL PREPARATION

CROSS-REFERENCE TO RELATED APPLICATION

This is a continuation of application Ser. No. 691,103, filed May 28, 1976, now U.S. Pat. No. 4,098,802, which application is a continuation-in-part of application Ser. No. 550,397, filed Feb. 18, 1975, now abandoned.

The invention relates to an oral pharmaceutical preparation having androgenic activity.

It is known to employ testosterone esters as androgenic substances in medicine, for instance in men with an insufficiency of endogenous androgens. These compounds are i.a. indicated in a retarded development of the external genitals of man, in eunuchoidism, in impotence on endocrine basis, after castration in man, in benign prostatic hypertrophy and in geriatry. The androgenic activity of testosterone ester is only revealed in the body after hydrolytic splitting off of the ester group. The ester form is used, however, to create a depot-effect and to prevent the quick metabolic decomposition of testosterone. Testosterone esters are therefore employed parenterally as so-called androgens with a prolonged activity. On application the esters are injected while dissolved or suspended in a suitable liquid carrier. The parenteral form of administration has its inconveniences. Usually a patient cannot give himself an injection and nearly always medical or nursing attendance is needed. Besides that a prolonged parenteral administration may cause local reactions. An oral administration form is far to be preferred therefore to the parenteral administration form.

It is known that testosterone shows only very little activity when administered orally. Probably it is quickly inactivated by the liver. From experiments it turned out that testogterone esterified with short chain aliphatic acids (1 to 5 carbon atoms) have also only a slight oral activity. A similar result was found on oral application of 5α-dihydrotestosterone and the short chain esters thereof.

Surprisingly it was found, however, that testosterone esters and 5α-dihydrotestosterone esters, derived from aliphatic carboxylic acids with 9 to 16 carbon atoms, when combined with a non-steroidal lipoids have a considerably stronger oral androgenic activity than esters derived from short chain aliphatic carboxylic acids. This is all the more surprising since the esters derived from an aliphatic carboxylic acid with more than 16 carbon atoms also turned out to have only a slight oral activity.

The invention therefore relates to an oral pharmaceutical preparation having androgenic activity which comprises at least one ester selected from the group consisting of esters of testosterone and 5α-dihydrotestosterone, the ester group of which being derived exclusively from an aliphatic carboxylic acid having 9-16 carbon atoms, and a pharaceutically acceptable carrier, said carrier comprising a non-steroidal lipoid.

The term "aliphatic carboxylic acid" also includes branched chain aliphatic and cycloaliphatic carboxylic acids.

The preparation according to the invention preferably comprises at least one testosterone ester and/or 5α-dihydrotestosterone ester derived from an aliphatic carboxylic acid having 10-12 C-atoms which esters turned out to possess the highest activity.

As examples of aliphatic carboxylic acids with 9-16 carbon atoms, from which the esters are derived, the following can be given: pelargonic acid, capric acid, undecanoic acid, lauric acid, tridecanoic acid, myristic acid, pentadecanoic acid, decenoic acid, undecenoic acid, palmitic acid and the branched chain and cyclic analogues of these acids such as α-(and β-)methyl-caprylic acid, α-(and β-)methyl-pelargonic acid, α-(and β-)methyl-capric acid, β,β-dimethyl-pelargonic acid, β-(p-methyl-cyclohexyl)-propionic acid, β-(β-ethyl-cyclohexyl)-propionic acid, β-(cycloheptyl)-propionic acid, α-(and β-)methyl-β-cyclohexyl propionic acid, cyclo-dodecyl-carboxylic acid, adamantane-1'-carboxylic acid, adamant-1'-yl-acetic acid and β-(bicyclo[2,2,-2]oct-1'-yl)-propionic acid. The ester is preferably derived from capric acid, undecanoic acid, lauric acid, tridecanoic acid, myristic acid or the α- or β-methyl-substituted or cyclic isomers of these acids.

Various of the testosterone and 5α-dihydrotestosterone esters indicated above are novel compounds. The present invention therefore also comprises novel esters with interesting androgenic properties, said novel esters having the formula:

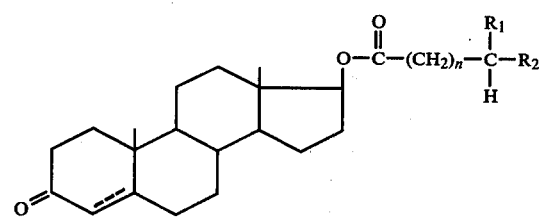

, wherein the dotted line indicates the optional presence of a double bond, said double bond preferably being present; n = 0 or 1, preferably 0; $R_1$ = methyl; $R_2$ = an aliphatic group having 5–18 C-atoms, preferably 6–12 C-atoms, when containing a cyclo-aliphatic group having 5–12 C-atoms, preferably 5–7 C-atoms, or an aliphatic group having 7–18 C-atoms, preferably 8–13 C-atoms, when not containing a cyclo-aliphatic group; or $R_1$ and $R_2$ form together with the C-atom to which they are attached a cyclo-aliphatic group having 7–12 C-atoms, said cyclo-aliphatic group optionally being substituted by an aliphatic group having 1–6 C-atoms, with the proviso that the total number of C-atoms in the ester group is in the range of 9–16 C-atoms and preferably 10–12 C-atoms.

Typical examples of the novel esters are the 17β-esters derived from α-methyl-capric acid, β-methyl-capric acid, α-methyl-β-cyclohexyl-propionic acid, β-cyclohexyl-butyric acid, β-cycloheptyl-propionic acid and β-cyclo-octyl-carboxylic acid.

The esters can be prepared according to methods known in the art, for example by reacting the steroid alcohol with the acid anhydride or with the acid chloride in the presence of pyridine.

By pharmaceutically acceptable non-steroidal lipoids are meant: the vegetable and animal oils and fats consisting of mono-, di- and triglycerides of various fatty acids or containing these glycerides as primary constituent; fatty acid esters of alcohols; higher aliphatic alcohols; saturated or unsaturated fatty acids; the commerically available synthetic and semi-synthetic mono-, di- and triglyceride oils and glycerol ether; certain types of wax and mixtures of two or more of the substances mentioned before.

The lipoid substance is preferably liquid at ambient temperature, that is, at a temperature in the range of about 10° C. to about 30° C. The testosterone- or 5α-dihydrotestosterone ester is then dissolved in the lipoid substance and the solution is processed in the preparation or processed to a pharmaceutical dosage unit form. Optionally, part of the ester is present in the liquid lipoid in suspended form at normal temperature, whereby the quantities of esters and lipoid substance have preferably been correlated such that the ester is fully dissolved in the lipoid substance at body-temperature.

Examples of lipoid substances which may be employed in the process according to the invention are: arachis oil, cstor oil, sesame oil, linseed oil, soya bean oil, sunflower seed oil, olive oil, fish liver oil, ethyl oleate, oleyl oleate, glyceryl trioleate, glyceryl dioleate, glyceryl-mono-oleate, cetyl alcohol, stearyl alcohol, capric acid, undecenoic acid, undecanoic acid, lauric acid, oleic acid, polyoxyethylene derivatives of glycerides, such as the trade product Labrafil 1944, synthetic glycerides of saturated fatty acids with 8 to 10 or 12 carbon atoms, such as the trade products Syndermin CTG and Miglyol 812, bee-wax and mixtures of two or more of these substances.

Preferred lipoid substances are the vegetable oils, such as arachis oil, castor oil, linseed oil and soja oil, further ethyl oleate, oleyl oleate, glyceryl mono-oleate, glyceryl trioleate and especially oleic acid.

The combination with non-steroidal lipoid substances has been based on the one side on the ability of the lipoid substances to increase the oral activity of the androgenic esters and on the other side on the solubility of the androgenic esters in the lipoid substance. With respct to the ability of the lipoid substances to increase the oral activity of the androgenic esters according to the invention it was found that the above preferred lipoid substances roughly possess about the same ability. With regard to the solubility of the androgenic esters in the above preferred lipoid substances it was determined that oleic acid has a high dissolving power, the solubility of for example testosterone undecanoate in the temperature range of 15° to 21° C. being in the range of 175 to 200 mg/ml. For the other preferred lipoid substances the solubility of for example testosterone undecanoate at about 20° C. is in the range of 75 to 150 mg/ml. The solubility is of importance, of course, in connecton with the desire of limiting the number of unit dosage forms that must be taken to cover the necessary daily intake of androgenic ester.

The present process provides an oral pharmaceutical preparation with androgenic activity. Contrary to other oral, androgenic pharmaceutical preparations, such as those containing methyltestosterone as active substance, the preparation according to the invention does not cause injuries to the liver. The invention also prevents the possibility to prepare an orally active, reversible male contraceptive by incorporating into the preparation also a substance that suppresses spermatogenesis. Such a substance has an inhibiting effect on the pituitary gland, owing to which the production of gonadotropic hormones is suppressed and/or has a direct inhibiting effect on the gonads. In this manner a state of oligospermatism or even azoospermatism is attained. This goes along with a lowering of the endogenous testosterone production owing to which also the testosterone level in the plasma is decreased. This may give cause for undesirable side effects, such as impotence and/or loss of libido. It has already been suggested to keep the plasma-testosterone level up to the mark by combining the oral administration of a substance suppressing spermatogenesis with an intramuscular injection of testosterone esters or a subcutaneous implantation that contains testosterone. In clinical trials satisfactory results were obtained with it. For application on a large scale this dosing methodology has considerable drawbacks as a matter of course.

As substance suppressing spermatogenesis an orally active progestative steroid can be employed. Thus by incorporating into the preparation according to the invention also an orally active progestative steroid a preparation is obtained with which by way of oral administration the spermatogenesis in man is decreased to an infertile level and the concurrent decrease of the plasma testosterone level is simultaneously compensated.

Examples of orally active progestative steroids are the (19-nor-)testosterone derivatives: 17α-ethynyl-$\Delta^4$-oestrene-17β-ol (lynestrenol), 17α-ethynyl-$\Delta^5$-oestrene-17β-ol (cingestol), 6α-methyl-17α-ethynyl-17β-hydroxy-$\Delta^4$-androsten-3-one (dimethisteron), 17α-ethynyl-17β-hydroxy-$\Delta^4$-oestrene-3-one (norethisteron) and the 17β-acetate of it, 17α-ethynyl-17β-hydroxy-$\Delta^{5(10)}$-oestren-3-one (nor-ethynodrel), 17α-ethynyl-17β-hydroxy-18-methyl-$\Delta^4$-oestren-3-one (nor-gestrel), 17α-ethynyl-$\Delta^4$-oestren-3β,17β-diol 3,17β-diacetate (ethynodiol diacetate), 17α-ethynyl-17β-hydroxy-$\Delta^{4,9,11}$-oestratrien-3-one and the corresponding 18-methyl-compound, 17α-ethynyl-17β-hydroxy-$\Delta^4$-oestreno-(2,3-d)-isoxazole (danazol), 7α-methyl-ethynodioldiacetate, 11β-chloro-lynestrenol, 11β-chloro-norethisteron, 7α-methyl-norgestrel and 11β-methyl-norethisterone, and the (19-nor-)-progesteron-derivatives: 6-chloro-17α-acetoxy-$\Delta^{4,6}$-pregnadiene-3,20-dione (chlormadinon acetate), 6-methyl-17α-acetoxy-$\Delta^{4,6}$-pregnadiene-3,20-dione (megestrol acetate), 6-methyl-16-methylene-17α-acetoxy-$\Delta^{4,6}$-pregnadiene-3,20-dione (melengestrolacetate), 9β,10α-$\Delta^{4,6}$-pregnadiene-3,20-dione (dydrogesteron), 6-chloro-9β,10α-$\Delta^{1,4,6}$-pregnatriene-3,20-dione, 17α-hydroxy-$\Delta^4$-pregnene-3,20-dione 17α-caproate and the corresponding 19-nor-compound, 6α-methyl-17α-acetoxy-$\Delta^4$-pregnene-3,20-dion (medroxyprogesterone acetate) and 17α-acetoxy-$\Delta^{4,6}$-19-nor-pregnadiene-3,20-dione.

Preferably a 3-desoxo-steroid of the oestrane series is employed as progestative steroid, such as lynestrenol, cingestol, 11β-chloro-lynestrenol and other 11β-substituted lynestrenols and 18-methyl-lynestrenols.

The invention also offers the possibility of preparing an oral pharmaceutical preparation having beside androgenic properties oestrogenic properties by incorporating into the preparation according to the invention an orally active oestrogen, such as 17α-ethinyl-oestradiol, mestranol or quinestrenol, or a precursor of an A-aromatic steroid such as 19-hydroxy-testosterone.

There is a want in medicine for such preparation having balanced androgenic/oestrogenic properties, in a number of indications, especially for climacteric complaints in women and men, for promoting a feeling of general well-being in post-climacteric women and men, for treating frigidity in women and impotence in men caused by a disturbance of the hormonal equilibrium in the body.

Thus, another embodiment of the invention is an oral pharmaceutical preparation comprising an ester of testosterone and/or 5α-dihydro-testosterone, the ester group of which has been derived exclusively from an aliphatic carboxylic acid having 9–16 carbon atoms, an oestrogen or a precursor of an A-aromatic steroid and a lipoid substance as defined before.

The preparation according to the invention can be administered orally in various dosage forms, for instance in the form of tablets, capsules, granules, pills, boluses, coated tablets, powders, granulates or microcapsules. Besides the androgenic ester(s) and the oily component and/or the progestative substance, the dosage forms may contain one or more of the usual excipients, for instance benzyl alcohol for enhancing the solubility of the active substance in the oil component, water, thickeners such as gelatin or agar-agar, polyethylene glycols, lactose, starch or magnesium stearate. If necessary also adjuvants may be present, such as preservatives, emulsifying agents, stabilisers, wetting agents, flavours, dyes, fillers, binding agents and/or coating agents.

The capsules may be soft or hard gelatin capsules, in which the active principle and the lipoid are present in granular or finely divided intimate admixture, in the form of a suspension in a liquid or in the form of an oily solution, if necessary even partly in suspension and partly in solution.

The combination of (5α-dihydro-)testosterone-17β-ester and lipoid, when liquid or semi-liquid, may also be processed to solid oral formulations such as pills or tablets. For that purpose the oily solution of the steroid ester is, for example, absorbed on calcium phosphate, lactose or cellulose derivatives and then processed to tablets or pills in the usual way. Combinations of the steroid esters of the invention with lipoids, such as glycerylmono-oleate or capric acid, which are solid or semi-solid at room temperature, may be granulated and processed to coated pills or tablets.

The most suitable oral administration form for this liquid form of the preparation according to the invention is the soft gelatine capsule or microcapsule. In accordance with a method usual in the technique, the oily solution containing the active components and optionally other ingredients is encapsulated to soft gelatine capsules or microcapsules with the desired dimensions and containing the desired amount(s) of active substances. The microcapusles can also be processed to tablets or pills according to well-known pharmaceutical formulation methods.

The androgenic ester(s) concentration in the preparation according to the invention can vary within considerable limits, on the understanding that the amount of androgenic ester(s) by weight does not exceed the amount of lipoid substance by weight or in other words the androgenic ester(s) concentration in the preparation is 50% by weight or less and is usually in the range of 1–40% by weight.

As indicated above, the amount of lipoid by weight in the preparation according to the invention is equal to or higher than the amount of androgenic ester by weight. Depending on the other constituents present in the preparation (excipients, capsule-shell, coating) the amount of lipoid substance per dosage unit will vary from 25 to 95% by weight and is usually in the range of 50–80% by weight. The amount of androgenic ester(s) per dosage unit, for example a capsule or a tablet, may also vary within wide limits, for example from 0.5 to 400 mg, and is preferably between 1 and 200 mg.

For practical reasons the amount of lipoid substance in the preparation is usually within the range of about 2 to 25 times the amount of androgenic ester (or esters) on a weight basis.

The quantity of progestative substance, used in the male contraceptive, depends on the potency of the substance in question and may vary betweeen 0.1 and 1000 mg and is preferably between 0.2 and 100 mg per unit dosage form. The amount of oestrogen or precursor of an A-aromatic steroid, if used in the preparation of the invention, depends on the potency of the substance in question and on the desired balance of androgen/oestrogen properties in the preparation and may vary between 0.002 and 2 mg for the oestrogen and between 0.1 and 500 mg for a precursor of an A-aromatic steroid, per unit dosage form.

The special biological properties of the novel preparations can be demonstrated for example by experiments in castrated rats (Hershberger test), wherein the increase in weight of the seminal vesicles and the ventral prostate is determined after having orally dosed the active substance for seven days once or twice a day.

In this way it turned out in such an experiment that with a daily oral dosage of 2×2 mg in arachis oil, the androgenic activity of testosterone, decanoate, testosterone undecanoate and testosterone dodecanoate was 2 to 3 times greater than that of testosterone, testosterone propionate, testosterone oenanthate, testosterone arachidate and testosterone behenate. Similar results were also found with the 5α-dihydro-testosterone esters.

In another experiment testosterone undecanoate (TU) was tested in various lipoids and without a lipoid (Table A).

Table A

| 2 × 2 mg/day/orally TU in | wt % (control = 100) | |
|---|---|---|
| | seminal vesicles | ventral prostate |
| sun-flower oil | 540 | 680 |
| Syndermin GTC | 550 | 690 |
| olive oil | 610 | 680 |
| tablet (crystalline form) | 270 | 460 |

Further tests according to Hershberger with 17-esters of testesterone and 5α-dihydrotestosterone derived from aliphatic carboxylic acids having X carbon atoms, after a daily oral administration of 2×1 mg in arachis oil for seven days, gave the results of Table B.

Table B

| X | wt % seminal vesicles (control = 100) | wt % ventral prostate (control = 100) |
|---|---|---|
| Testosterone esters | | |
| 5 | 150 | 370 |
| 7 | 190 | 360 |
| 9 | 290 | 510 |
| 10 | 380 | 670 |
| 11 | 420 | 620 |
| 12 | 260 | 460 |
| 13 | 205 | 420 |
| 16 | 200 | 430 |
| 18 | 175 | 390 |
| 5α-Dihydrotestosterone esters | | |
| 0 | 226 | 270 |
| 3 | 212 | 316 |
| 5 | 166 | 277 |
| 8 | 225 | 290 |
| 10 | 322 | 442 |
| 11 | 420 | 412 |
| 12 | 346 | 365 |
| 16 | 262 | 308 |

The data of Table B indicate that the oral pharmaceutical preparations according to the invention have very strong androgenic properties. When the weight percentage of testosterone and 5α-dihydrotestosterone in the esters (testosterone and 5α-dihydrotestosterone being the active constituent in the esters thereof) is taken into account then the activities are even higher and grow relatively higher as X increases.

In another comparative test (Hershberger test) testosterone (T), testosterone decanoate (T 10) and testosterone dodecanoate (T 12) were tested in crystalline form (A) and in arachis oil (B) at a daily oral dose of 2×2 mg for seven days (Table C).

Table C

| Compound | Oral dosage form | wt % sem. ves. (control = 100) | wt % ventr. prost. (control = 100) |
|---|---|---|---|
| T | A | 180 | 350 |
| T | B | 230 | 370 |
| T 10 | A | 320 | 390 |
| T 10 | B | 560 | 670 |
| T 12 | A | 270 | 290 |
| T 12 | B | 510 | 610 |

The data of Table C clearly demonstrate the positive influence of the lipoid in the oral pharmaceutical preparation according to the invention, whereas for testosterone itself there is hardly any influence.

A comparative test including branched chain esters gave the results illustrated in Table D (Hershberger test).

Table D

| Testosterone ester (orally in arachis oil) | wt % seminal vesicles (control = 100) | wt % ventral prost. (control = 100) |
|---|---|---|
| decanoate | 310 | 590 |
| α-methyl-β-cyclohexyl-propionate | 770 | 730 |
| β-cyclohexyl-butyrate | 680 | 750 |
| undecanoate | 340 | 560 |
| α-methyl-decanoate | 790 | 700 |
| β-methyl-decanoate | 620 | 710 |

The data of Table D illustrate the remarkable increase in activity by α-methyl and β-methyl substitution of the ester group.

In clinical trials with preparations according to the invention, wherein a daily dose of testosterone ester in the range from 50 to 200 mg was administered, a considerable increase of the plasmatestosterone level was found both in men with a normal plasmatestosterone level and in men with a lower level resulting from a decreased production of endogenous testosterone.

A clinical trial with a daily oral dose of 80 mg testosterone undecanoate in 0.5 ml oleic acid (two soft gelatine capsules of 40 mg ester in 0.24 ml oleic acid) for three months in a hypogonadal man gave a remarkable improvement in his libido and his sexual, physical and mental activities. The plasmatestosterone level was markedly increased from 50 ng/100 ml to 200 ng/100 ml.

The clinical trails indicate that the use of the oral preparations according to the invention is an effective form of androgen substitution therapy in hypogonadal male patients.

Therefore it is shown by the above disclosure that an effective method for conducting androgen deficiency therapy in a male patient requiring such therapy comprises orally administering daily to said patient from 0.5 to 400 mg of the ester or esters of testosterone and 5α-dihydrotestosterone mentioned above, together with a non-steroidal lipoid substance, the amount of said lipoid substance being equal to or higher than the amount of said ester or esters, and preferably from about 2 to about 25 times the amount of said ester or esters.

The invention is illustrated with the following examples:

EXAMPLE I

Soft gelatine capsules

A sterile solution of testosterone undecanoate in arachis oil was made, containing 41.67 g per liter. Under aseptic conditions this solution was encapsulated, according to the usual soft gel encapsulating technique. In this manner soft gelatine capsules were obtained with a content of 0.24 ml so that the content of active substance per capsule was 10 mg. The wall of the capsule (113 mg) consisted of 77 mg of gelatine, 17.5 mg of glycerol, 15.5 mg of sorbitol, 0.5 mg of sodium-para-hydroxy-benzoic acid ethyl/propyl ester, 0.6 mg of $TiO_2$ and 1.9 mg of Cochineal red A (dye).

In the same manner testosterone caprate, testosterone α-methylcaprate, 5α-dihydro-testosterone laurate and testosterone myristate were processed into soft gelatine capsules, containing 10 mg of active substance in arachis oil (0.24 ml).

EXAMPLE II

Soft gelatine capsules

A sterile solution was made of testosterone undecanoate in glyceryl trioleate, containing 80.64 g per liter. In the manner as indicated in example I, this solution was encapsulated. Soft gelatine capsules were obtained with a content of 0.31 ml, containing 25 mg of testosterone undecanoate. In a similar manner testosterone pelargonate was encapsulated into soft gelatine capsules containing 0.31 ml of a solution of 35 mg of the ester in ethyl oleate, and a mixture of equal portions of testosterone caprate and testosterone laurate was encapuslated into soft gelatine capsules, containing 0.31 ml of a solution of 20 mg of the ester-mixture in glyceryl trioleate.

EXAMPLE III

| Tablets | |
|---|---|
| Testosterone undecanoate | 25 mg |
| Undecanoic acid | 50 mg |
| Lactose | 145 mg |
| Potato starch | 28 mg |
| Magnesium stearate | 2 mg |
| | 250 mg |

While gently heating, the testosterone undecanoate was dissolved in the undecanoic acid, whereafter this solution was absorbed homogeneously in the lactose. After mixing with potato starch and a little water, the thus obtained granulate was dried. The dry granulate was mixed with magnesium stearate as lubricant and tabletted in the usual manner.

In a similar manner tablets of the following composition were manufactured:

| | |
|---|---|
| 5α-Dihydrotestosterone laurate | 25 mg |
| Lynestrenol | 5 mg |
| Methyl cellulose | 15 mg |
| Glyceryl mono-oleate | 88 mg |
| Lactose | 115 mg |
| Magnesium stearate | 2 mg |
| | 250 mg |

EXAMPLE IV

| Hard gelatin capsules | |
|---|---|
| Testosterone undecanoate | 100 mg |
| Stearyl alcohol | 375 mg |
| Norethisteron | 25 mg |
| | 500 mg |

Testosterone undecanoate is dissolved at 60° C. in stearyl alcohol. After cooling the solid mixture is triturated and thoroughly mixed with norethisteron. With the mixture thus obtained, hard gelatine capsules are dispensed.

EXAMPLE V

A sterile solution of testosterone undecanoate in oleic acid was made, containing 166.67 g per liter. In the manner as indicated in example I, this solution was encapsulated to soft gelatine capsules with a content of 0.18 ml, thus containing 30 mg of the testosterone ester per capsule.

In a similar manner testosterone α-methyl-β-cyclohexylpropionate in oleic acid was encapsulated to soft gelatine capsules with a content of 0.18 ml, containing 20 mg of the ester per capsule.

EXAMPLE VI

Testosterone undecanoate was dissolved in undecanoic acid at 30° C. The solution contained 277.78 g ester per liter. This soluton was encapsulated to soft gelatine capsules with a content of 0.18 ml, thus containing 50 mg of ester per capsule.

EXAMPLE VII

Preparation of novel esters

To a solution of 2 g testosterone in a mixture of 8 ml pyridine and 8 ml acetone, cooled to $-10°$ C., was added dropwise in a nitrogen atmosphere a solution of 4 ml α-methyl-decanoyl-chloride in 12 ml acetone. The mixture was stirred for 16 hours at 0° C., whereafter 4 ml pyridine and 8 ml water were added to the mixture. The mixture was stirred for 1 hour at 0° C. and 2 hours at 45° C. and then poured out in 200 ml ice-water. Extraction with diethylether neutralisation of the extracts, evaporation of the diethylether and chromatography of the residue on silicagel with toluene/ethylacetate 8/2 gave 3.0 g testosterone α-methyl-caprate in the form of an oil with $[\alpha]_D^{20} = +77.0°$ (in methylenechloride) and $\epsilon_{mol}$ 16.800 ($\lambda_{max}$ 240 m$\mu$).

In a similar manner the following 17β-esters were prepared:
testosterone β-methyl-caprate
testosterone α-methyl-β-cyclohexylpropionate
testosterone β-cyclohexyl-butyrate
testosterone β-cycloheptyl-propionate
testosterone cyclododecylcarboxylate
5α-dihydrotestosterone α-methylcaprate.

We claim:

1. A pharmaceutical composition with androgenic activity adapted for oral administration, in unit dosage form, comprising, per dosage unit:
   (a) an androgenically effective amount of at least one ester selected from the group consisting of esters of testosterone and 5α-dihydrotestosterone, the ester group which has been derived exclusively from an aliphatic carboxylic acid having 9–16 carbon atoms; and
   (b) a pharmaceutically acceptable carrier, said carrier comprising a pharmaceutically acceptable non-steroidal lipoid substance, wherein said lipoid substance is present in an amount equal to or higher than the amount of said ester or esters.

2. The composition of claim 1 wherein said ester has been derived from an aliphatic carboxylic acid having 10–12 carbon atoms.

3. The composition of claim 1 wherein said ester has been derived from an aliphatic carboxylic acid being α-substituted by a methyl group.

4. The composition of claim 1 wherein said lipoid carrier is liquid at ambient temperature.

5. The composition of claim 1 wherein said lipoid substance constitutes from about 25% to about 95% by weight of said preparation.

6. The composition of claim 1 wherein said lipoid substance is present in an amount by weight within the range from about 2 to about 25 times the amount by weight of said ester or esters.

7. A process for conducting androgen deficiency therapy in a male patient requiring such therapy comprising orally administering daily, in unit dosage form, per dosage unit, to said patient from 0.5 to 400 mg of one or more esters selected from the group consisting of esters of testosterone and 5α-dihydrotestosterone, the ester group which has been derived exclusively from an aliphatic carboxylic having 9–16 carbon atoms, which ester or esters comprise a composition with a pharmaceutically acceptable carrier, said carrier comprising a pharmaceutically acceptable non-steroidal lipoid substance, wherein said lipoid substance is present in an amount equal to or higher than the amount of said ester or esters.

8. The process of claim 7 wherein the amount by weight of said lipoid substance is within the range from about 2 to about 25 times the amount by weight of said ester or esters.

9. A pharmaceutical composition, in unit dosage form, with androgenic activity adapted for oral administration for the suppression of spermatogenisis which comprises:
   (a) an amount of at least one ester effective to suppress spermatogenisis selected from the group consisting of esters of testosterone and 5α-dihydrostestosterone, the ester group of which has been derived exclusively from an aliphatic carboxylic acid having 9–16 carbon atoms;
   (b) a pharmaceutically acceptable carrier, said carrier comprising a pharmaceutically acceptable non-steroidal lipoid substance, in unit dosage form comprising, per dosage unit, wherein said lipoid substance is present in an amount equal to or higher than the amount of said ester or esters; and
   (c) an effective amount of an orally active progestative steroid.

10. A pharmaceutical composition, in unit dosage form, with androgenic and oestrogenic properties adapted for oral administration which comprises:
   (a) an amount of at least one ester effective to suppress spermatogenisis selected from the group consisting of esters of testosterone and 5α-dihydrotestosterone, the ester group of which has been derived exclusively from an aliphatic carboxylic acid having 9–16 carbon atoms;

(b) a pharmaceutically acceptable carrier, said carrier comprising a pharmaceutically acceptable non-steroidal lipoid substance, in unit dosage form comprising, per dosage unit, wherein said lipoid substance is present in an amount equal to or higher than the amount of said ester or esters; and (c) an effective amount of one or more of the group consisting of oestrogen and precursors of an A-aromatic steroid.

11. A composition recited in claim 1, wherein the pharmaceutically acceptable non-steroidal lipoid substance is selected from the group consisting of (1) the vegetable and animal oils and fats consisting of mono-, di- and triglycerides of various fatty acids or containing these glycerides as primary constituent; (2) fatty acid esters or alcohols, higher aliphatic alcohols; (3) saturated or unsaturated fatty acids, higher aliphatic alcohols; (4) the commercially available synthetic and semi-synthetic mono-, di and triglyceride oils and glycerol ethers; and (5) certain types of wax.

* * * * *